(12) United States Patent
Hyeon

(10) Patent No.: US 11,619,729 B2
(45) Date of Patent: *Apr. 4, 2023

(54) ULTRASOUND APPARATUS AND CONTROL METHOD THEREOF

(71) Applicant: SAMSUNG MEDISON CO., LTD., Gangwon-do (KR)

(72) Inventor: Yong-Cheol Hyeon, Seoul (KR)

(73) Assignee: SAMSUNG MEDISON CO., LTD., Gangwon-Do (KR)

( * ) Notice: Subject to any disclaimer, the term of this patent is extended or adjusted under 35 U.S.C. 154(b) by 1142 days.

This patent is subject to a terminal disclaimer.

(21) Appl. No.: 16/178,472

(22) Filed: Nov. 1, 2018

(65) Prior Publication Data

US 2019/0129021 A1 May 2, 2019

Related U.S. Application Data

(60) Provisional application No. 62/580,350, filed on Nov. 1, 2017.

(30) Foreign Application Priority Data

Apr. 9, 2018 (KR) .................. 10-2018-0040980

(51) Int. Cl.
*G01S 7/52* (2006.01)
*A61B 8/00* (2006.01)
(Continued)

(52) U.S. Cl.
CPC ............ *G01S 7/5205* (2013.01); *A61B 8/461* (2013.01); *G01S 7/52077* (2013.01);
(Continued)

(58) Field of Classification Search
CPC ............... G01S 7/5205; G01S 7/52077; G01S 7/52085; G01S 7/52076; G01S 7/52017; A61B 8/461; H01L 41/00; H01L 41/042
See application file for complete search history.

(56) References Cited

U.S. PATENT DOCUMENTS 11,215,702 B2 * 1/2022 Hyeon .................. A61B 8/461
2004/0004905 A1 1/2004 Lyon et al.
(Continued)

FOREIGN PATENT DOCUMENTS

EP 3 335 636 A1 6/2018
JP 2005-318966 A 11/2005
(Continued)

OTHER PUBLICATIONS

Search Report issued in corresponding European Application No. 18203581.6, dated Mar. 7, 2019.

*Primary Examiner* — Yi-Shan Yang
*Assistant Examiner* — Nicholas A Robinson
(74) *Attorney, Agent, or Firm* — Morgan, Lewis & Bockius LLP

(57) ABSTRACT

Provided is an ultrasound apparatus including: a transmitter configured to generate and output a transmission signal; an ultrasound probe configured to convert the transmission signal output from the transmitter into an ultrasound signal and transmit the ultrasound signal to a target object, and receive an echo signal reflected from the target object and output a reception signal on the basis of the echo-signal; a transmission/reception switch configured to attenuate the transmission signal output from the transmitter and output the attenuated transmission signal, and output the reception signal output from the ultrasound probe; and a receiver configured to receive the attenuated and output transmission signal and the output reception signal, and detect transmission waveform information on the basis of the attenuated transmission signal.

20 Claims, 14 Drawing Sheets

(51) Int. Cl.
   *H01L 41/00*    (2013.01)
   *H01L 41/04*    (2006.01)
(52) U.S. Cl.
   CPC .......... *G01S 7/52085* (2013.01); *H01L 41/00* (2013.01); *H01L 41/042* (2013.01); *G01S 7/52076* (2013.01)

(56) References Cited

U.S. PATENT DOCUMENTS

| | | | |
|---|---|---|---|
| 2006/0061231 | A1 | 3/2006 | Kameishi |
| 2008/0225639 | A1 | 9/2008 | Hongou |
| 2010/0228128 | A1* | 9/2010 | Lee .................. A61B 8/461 |
| | | | 600/443 |
| 2012/0013404 | A1* | 1/2012 | Ngai .................. H03F 1/3205 |
| | | | 330/254 |
| 2016/0183927 | A1 | 6/2016 | Krmsl et al. |
| 2016/0296209 | A1* | 10/2016 | Lee .................. A61B 8/00 |
| 2019/0129021 | A1* | 5/2019 | Heyon .............. G01S 7/52077 |
| 2020/0256969 | A1* | 8/2020 | Hyeon .............. G01S 7/52087 |

FOREIGN PATENT DOCUMENTS

| | | |
|---|---|---|
| JP | 2010-268852 A | 12/2010 |
| JP | 2011-229630 A | 11/2011 |
| WO | 2017/065562 A1 | 4/2017 |

* cited by examiner

ULTRASOUND APPARATUS AND CONTROL METHOD THEREOF

CROSS-REFERENCE TO RELATED APPLICATION

This application is based on and claims priority under 35 U.S.C. § 119 to U.S. Patent No. 62/580,350, filed on Nov. 1, 2017, in the U.S. Patent and Trademark Office, and Korean Patent Application No. 10-2018-0040980, filed on Apr. 9, 2018 in the Korean Intellectual Property Office, the disclosures of which are incorporated herein by reference.

BACKGROUND

1. Field

The present disclosure relates to an ultrasound apparatus in which whether the ultrasound apparatus operates normally is determined in real time by detecting a waveform of a transmission signal generated from the ultrasound apparatus, and a control method thereof.

2. Description of the Related Art

The present disclosure relates to an ultrasound apparatus for determining whether the ultrasound apparatus operates normally by detecting a waveform of a transmission signal An ultrasound apparatus is an apparatus for obtaining an internal image of a subject by irradiating an ultrasound signal, having been generated from a transducer of an ultrasound probe, through the skin of the body of the subject toward a target site inside the subject and receiving information about an ultrasound signal (an ultrasound echo signal) from the subject.

The ultrasound apparatus has high safety without radiation exposure as compared to an X-ray diagnosis apparatus, executes display in real time, is inexpensive as compared to a magnetic resonance image (MRI), and has a mobility, thus the ultrasound apparatus is widely used in the field of medical diagnostics.

SUMMARY

Therefore, it is an object of the present disclosure to provide an ultrasound apparatus capable of detecting a transmission waveform without an additional reception channel when detecting waveforms of transmission signals output by the ultrasound apparatus, and a control method thereof.

Additional aspects of the invention will be set forth in part in the description which follows and, in part, will be obvious from the description, or may be learned by practice of the invention.

Therefore, it is an aspect of the present invention to provide an ultrasound apparatus including: a transmitter configured to generate and output a transmission signal; an ultrasound probe configured to convert the transmission signal output from the transmitter into an ultrasound signal and transmit the ultrasound signal to a target object, and receive an echo signal reflected from the target object and output a reception signal on the basis of the echo-signal; a transmission/reception switch configured to attenuate the transmission signal output from the transmitter and output the attenuated transmission signal, and output the reception signal output from the ultrasound probe; and a receiver configured to receive the attenuated and output transmission signal and the output reception signal, and detect transmission waveform information on the basis of the attenuated transmission signal.

The transmission/reception switch may include: a switching module configured to block the transmission signal from being transmitted to the receiver and allow the reception signal to be transmitted to the receiver; and a resistor element configured to attenuate the transmission signal.

The switching module may include a diode bridge switchable between a first state and a second state.

The switching module may block the transmission signal from being transmitted to the receiver by applying a reverse bias current to the diode bridge in the first state, and allow the reception signal to be transmitted to the receiver by applying a forward bias current to the diode bridge in the second state.

The switching module may include at least one switch that is switchable between a first state and a second state.

The switching module may control the at least one switch to operate in one of a short-circuit state and an open-circuit state, to block the transmission signal from being transmitted to the receiver in the first state and allow the transmission signal to be transmitted to the receiver in the second state.

The transmission/reception switch may be configured to: disable the switching module in a first section such that the transmission signal is attenuated through the resistor element and is transmitted to the receiver; and enable the switching module in a second section such that the reception signal is transmitted to the receiver through the switching module, wherein the first section is a section in which the transmitter outputs the transmission signal, and the second section is a section in which the ultrasound probe outputs the reception signal.

The attenuated transmission signal may have a voltage that is defined as Equation 1, in which the voltage of the attenuated transmission signal falls within an input range of the receiver:

$$V_s' = V_s \times \frac{R_{in}}{R_s + R_{in}}, \quad \text{[Equation 1]}$$

in Equation 1, $V_s'$ denotes a voltage of the attenuated transmission signal, $V_s$ denotes a voltage of the transmission signal, $R_{in}$ denotes an input impedance of the receiver, and $R_s$ denotes a resistance value of the resistor element.

The transmission waveform information may include at least one of a waveform of the transmission signal, an amplitude of the transmission signal, and information about a generation time of the transmission signal based on a synchronization signal.

The ultrasound apparatus may further include a display; and a controller configured to store reference waveform information according to a transmission condition, and compare the detected transmission waveform information with the reference waveform information.

The controller, when the detected transmission waveform information is different from the reference waveform information, may control the display to notify a user of an abnormality, or stops operating the ultrasound apparatus.

The controller, when the detected transmission waveform information is different from the reference waveform information, may correct the transmission signal corresponding to the detected transmission waveform information.

The controller may compare transmission waveform information corresponding to the corrected transmission signal with the reference waveform information.

The controller, when the transmission waveform information is different from the reference waveform information, may control the display to notify a user of an abnormality, or stop operating the ultrasound apparatus.

The controller may control the display to display the detected transmission waveform information.

One end of the transmission/reception switch may be connected to the transmitter and the ultrasound probe, and an opposite end of the transmission/reception switch may be connected to the receiver.

It is another aspect of the present invention to provide a method of controlling an ultrasound apparatus including a ultrasound probe and a transmission/reception switch, the method including: receiving a transmission signal output from a transmitter and a reception signal output from the ultrasound probe by controlling the transmission/reception switch; outputting the transmission signal attenuated by a resistor element by controlling the transmission/reception switch; outputting the reception signal through a switching module by controlling the transmission/reception switch; receiving the attenuated and output transmission and the output reception signal by controlling the receiver; and detecting transmission wave information on the basis of the attenuated transmission signal by controlling the receiver.

The method may include: disabling the switching module in a first section such that the transmission signal is attenuated through the resistor element and is transmitted to the receiver; and enabling the switching module in a second section such that the reception signal is transmitted to the receiver through the switching module, wherein the first section may be a section in which the transmitter outputs the transmission signal, and the second section may be a section in which the ultrasound probe outputs the reception signal.

The attenuated transmission signal may have a voltage that is defined as Equation 1, in which the voltage of the attenuated transmission signal falls within an input range of the receiver:

$$V_s' = V_s \times \frac{R_{in}}{R_s + R_{in}} \quad \text{[Equation 1]}$$

in Equation 1, $V_s'$ denotes a voltage of the attenuated transmission signal, $V_s$ denotes a voltage of the transmission signal, $R_{in}$ denotes an input impedance of the receiver, and $R_s$ denotes a resistance value of the resistor element.

The transmission waveform information may include at least one of a waveform of the transmission signal, an amplitude of the transmission signal, and information about a generation time of the transmission signal based on a synchronization signal.

The method may further include storing reference waveform information according to a transmission condition; and comparing the detected transmission waveform information with the reference waveform information.

The method may include, when the detected transmission waveform information is different from the reference waveform information, controlling a display to notify a user of an abnormality; and stopping operating the ultrasound apparatus.

The method may include, when the detected transmission waveform information is different from the reference waveform information, correcting the transmission signal corresponding to the detected transmission waveform information.

The method may include comparing transmission waveform information corresponding to the corrected transmission signal with the reference waveform information.

The method may include, when the transmission waveform information is different from the reference waveform information, controlling the display to notify a user of an abnormality, or stopping operating the ultrasound apparatus.

The method may include controlling the display to display the detected transmission waveform information.

BRIEF DESCRIPTION OF THE DRAWINGS

These and/or other aspects of the invention will become apparent and more readily appreciated from the following description of the embodiments, taken in conjunction with the accompanying drawings of which.

DETAILED DESCRIPTION

Figure 1:
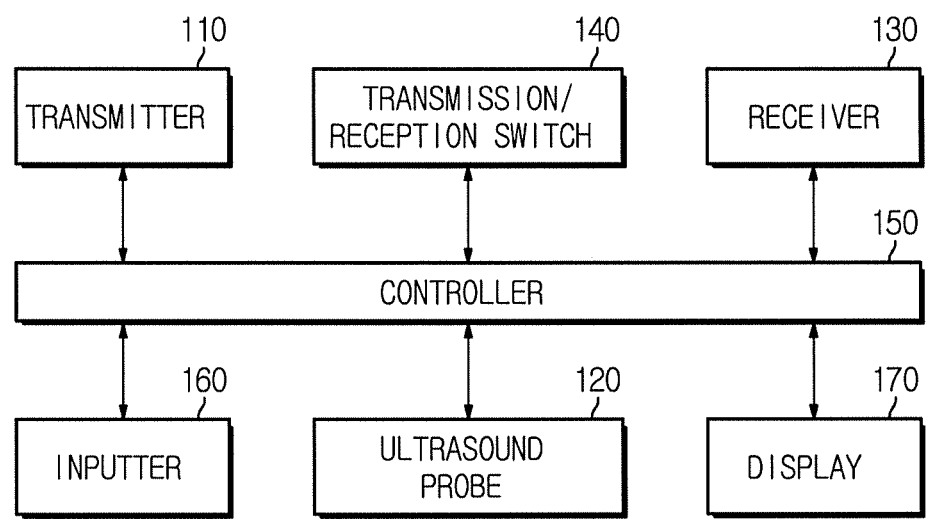
FIG. 1 is a control block diagram illustrating an ultrasound apparatus according to an embodiment of the present disclosure.

Like numerals refer to like elements throughout the specification. Not all elements of embodiments of the present disclosure will be described, and description of what are commonly known in the art or what overlap each other in the embodiments will be omitted. The terms as used throughout the specification, such as "~part", "~module", "~member", "~block", etc., may be implemented in software and/or hardware, and a plurality of "~parts", "~modules", "~members", or "~blocks" may be implemented in a single element, or a single "~part", "~module", "~member", or "~block" may include a plurality of elements.

It will be further understood that the term "connect" or its derivatives refer both to direct and indirect connection, and the indirect connection includes a connection over a wireless communication network.

It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof, unless the context clearly indicates otherwise.

Further, it will be further understood when a signal or data is transferred, sent or transmitted from "an element" to "another element", it does not exclude another element between the element and the other element passed by the signal or data therethrough, unless the context clearly indicates otherwise.

Although the terms "first," "second," "A," "B," etc. may be used to describe various components, the terms do not limit the corresponding components, but are used only for the purpose of distinguishing one component from another component.

As used herein, the singular forms "a," "an" and "the" are intended to include the plural forms as well, unless the context clearly indicates otherwise.

Reference numerals used for method steps are just used for convenience of explanation, but not to limit an order of the steps. Thus, unless the context clearly dictates otherwise, the written order may be practiced otherwise.

Hereinafter, embodiments of an ultrasound apparatus and a control method thereof according to one aspect will be described in detail with reference to the accompanying drawings.

Figure 2:
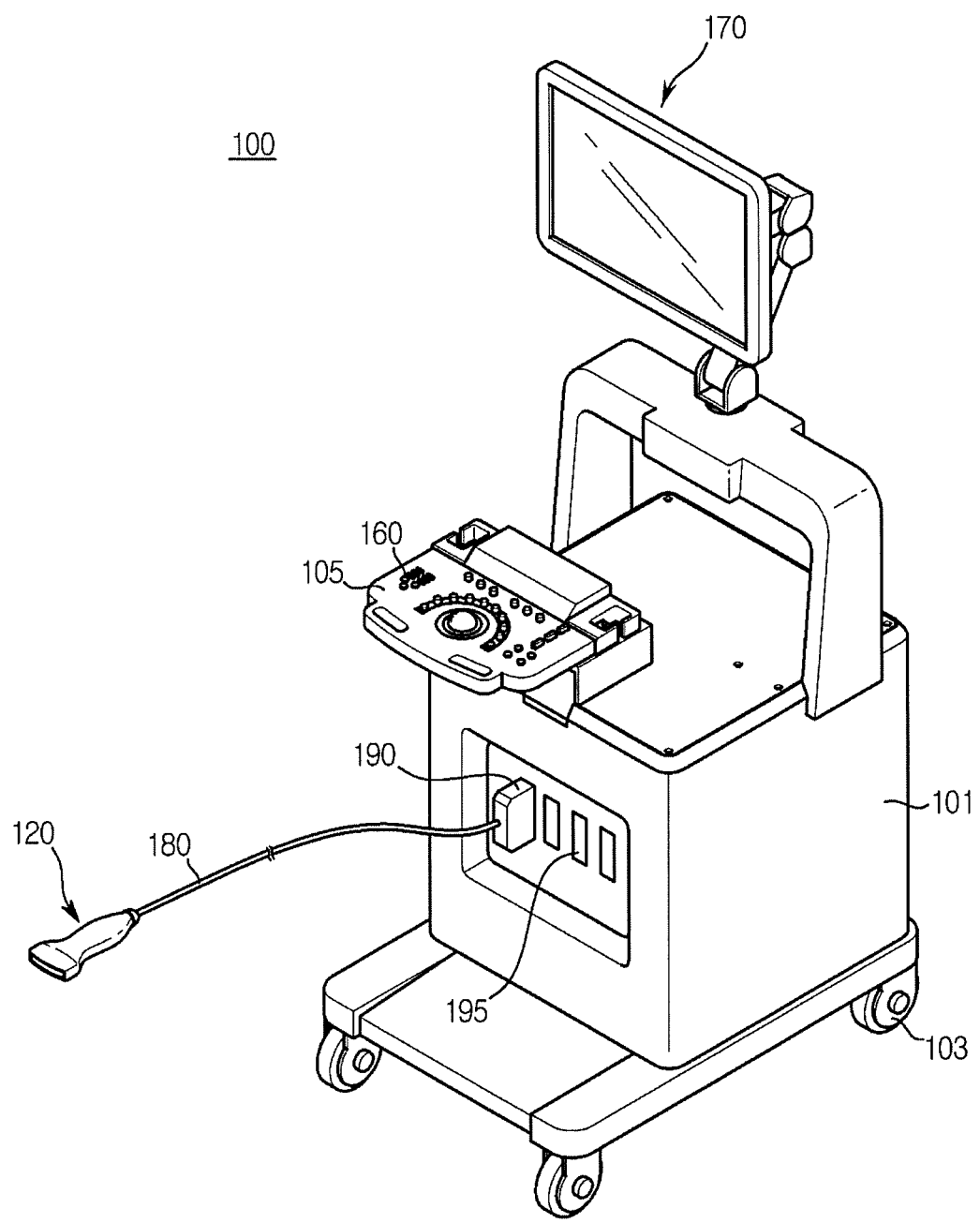
FIG. 2 is an external view illustrating an ultrasound apparatus according to an embodiment.

FIG. 1 is a control block diagram illustrating an ultrasound apparatus according to an embodiment, and FIG. 2 is an external view of an ultrasound apparatus according to an embodiment.

Referring to FIGS. 1 and 2, an ultrasound apparatus 100 according to an embodiment includes a transmitter 110 for outputting a transmission signal to be converted into an ultrasound signal in an ultrasound probe 120, the ultrasound probe 120 for transmitting the ultrasound signal to a target object, receiving an ultrasound echo signal reflected from the target object and outputting a reception signal on the basis of the ultrasound echo signal, a transmission/reception switch 140 for attenuating and transmitting the transmission signal while transmitting the reception signal without attenuation, a controller 150 for controlling the operation of the internal components of the ultrasound apparatus 100, an inputter 160, and a display 170.

The transmitter 110 may output a transmission signal for obtaining frames of an ultrasound image. The transmission signal output by the transmitter 110 may correspond to an electrical signal. The frames of the ultrasound image may include an A-mode (Amplitude mode) frame, a B-mode (Brightness mode) frame, a C-mode (color mode) frame, a D-mode (Doppler mode) frame, an E-mode (Elastography mode) frame, a M-mode (Motion mode) frame, an elasticity image frame, and the like.

In detail, the transmitter 110 may output a transmission signal according to a control signal of the controller 150. The transmitter 110 may output a transmission signal at a time delay set with reference to a synchronization signal having a pulse repetition frequency (PRF). Accordingly, the transmission signal generated by the transmitter 110 may be a pulse having a PRF.

The transmitter 110 may have a plurality of transmission channels to output a plurality of transmission signals. In detail, the transmitter 110 may have a plurality of transmission channels each connected to a plurality of transducers on the ultrasound probe 120, and may transmit each transmission signal to the transducer through a corresponding one of the plurality of transmission channels.

The transmission signal of the transmitter 110 may be provided using a high voltage signal. In detail, the voltage of the transmission signal may have a maximum level of 200 Vp-p. The reception signal output by the ultrasound probe 120 on the basis of an ultrasound echo signal reflected from a target object corresponds to a low-voltage signal as compared to the transmission signal of the transmitter 110. Therefore, in general, the receiver 130 of the ultrasound apparatus 100 may use a range of the voltage of the reception signal of the ultrasound probe 120 as an input range.

The ultrasound probe 120 is a portion that makes contact with the surface of the body of the target object or is inserted into the body, and is configured to transmit and receive ultrasound waves. In detail, the ultrasound probe 120 converts a transmission signal into an ultrasound signal according to the transmission signal provided from the transmitter 110, transmits ultrasound wave to the interior of the target object, receives an ultrasound echo signal reflected from a particular site inside the target object, converts the ultrasound echo signal into a reception signal, which is an electrical signal, and transmits the reception signal to the receiver 110.

To this end, the ultrasound probe 120 may include a transducer and a MUX circuit. The transducer may include a plurality of elements that vibrate to convert an electrical signal into ultrasound waves, or to convert ultrasound waves to an electrical signal. The plurality of elements may be arranged on one side of a housing of the ultrasound probe. In detail, a plurality of transducers may be arranged in a direction parallel to an opening provided at one side of the housing such that ultrasound waves are transmitted and received through the opening. The ultrasound probe 120 may convert a transmission signal into an ultrasound signal or convert a ultrasound echo signal into a reception signal using the transducer.

The transducer of the ultrasound probe 120 may be implemented as a piezoelectric ultrasound transducer using a piezoelectric effect. To this end, the transducer may include a piezoelectric material or a piezoelectric thin film. When an alternating current is applied to the piezoelectric material or piezoelectric thin film from an internal power storage device, such as a battery, or an external power supply device, the piezoelectric material or piezoelectric thin film vibrates at a predetermined frequency, and thus generates an ultrasound wave of a predetermined frequency corresponding to the vibration frequency.

On the other hand, when an ultrasound echo signal of a predetermined frequency reaches the piezoelectric material or the piezoelectric thin film, the piezoelectric material or the piezoelectric thin film vibrates according to the frequency of the echo ultrasound waves that have reached the piezoelectric material or the piezoelectric thin film, and the piezoelectric material or the piezoelectric thin film outputs an alternating current corresponding to the vibration frequency.

The transducer of the ultrasound probe 120 may be implemented as other types of transducer, e.g., a magnetostrictive ultrasound transducer using magnetostrictive effect of a magnetic body, or a capacitive micromachined ultrasound transducer (cMUT) that transmits and receives ultrasound waves using vibrations of several hundreds or thousands of micromachined thin films.

Each of the plurality of transducers of the ultrasound probe 120 may be connected to a corresponding one of the plurality of transmission channels of the transmitter 110 to receive a transmission signal output from the transmitter 110. Each of the plurality of transducers of the ultrasound probe 120 may also be connected to a corresponding one of the plurality of reception channels of the receiver 130 to transmit the reception signal to the receiver 130.

The ultrasound probe 120 is connected to a main body 101 through a cable 180 or using a wireless communication network to receive various signals required for controlling the ultrasound probe 120 from the transmitter 110 built in the main body 101, or transmit a reception signal corresponding to an ultrasound echo signal received by the ultrasound probe 120 to the receiver 130 built in the main body 101.

The receiver 130 may receive the reception signal output from the ultrasound probe 120 to detect an ultrasound image. In detail, the receiver 130 may include an amplifier for amplifying an input signal, an analog-to-digital converter (ADC) for converting an input signal into a digital signal, and a digital signal processor. The receiver 130 amplifies the reception signal, converts the reception signal into a digital signal, and processes the reception signal, thereby detecting the ultrasound image. That is, the receiver 130 converts a plurality of reception signals received through the plurality of reception channels into digital signals, receives and focuses the plurality of reception signals in the digital form, and detect an ultrasound image using the plurality of received and focused reception signals.

Since the receiver 130 is provided to receive and process the reception signal output from the ultrasound probe 120, the voltage input range of the receiver 130 generally employs the voltage range of the reception signal. Accordingly, the receiver 130 has a difficulty in receiving the high-voltage transmission signal output from the transmitter 110 without distortion. Further, when receiving a transmission signal of a high voltage exceeding the input range of the receiver, the receiver may be broken. Accordingly, in the conventional ultrasound apparatus, a switch is disposed between the transmitter and the receiver to block a high-voltage transmission signal output from the transmitter from being transmitted to the receiver, thereby minimizing the transmission of the transmission signal to the receiver.

The transmission/reception switch 140 includes the conventional switch as it is, but add a resistor element to attenuate a transmission signal output from the transmitter 110 and transmit the attenuated transmission signal to the receiver 130. The transmission/reception switch 140 may attenuate the transmission signal output from the transmitter 110 and transmit the attenuated signal to the receiver 130, and may transmit the reception signal output from the ultrasound probe 120 to the receiver 130 without attenuation. Since the transmission signal is attenuated and transmitted to the receiver 130, the receiver 130 may receive the transmission signal without distortion and the receiver 130 is prevented from being broken.

In detail, the transmission/reception switch 140 attenuates the transmission signal transmitted from the transmitter 110 and transmits the attenuated transmission signal to the receiver 130 in a transmitting section in which the transmitter 110 outputs the transmission signal. The transmission signal is attenuated not to exceed the input range of the receiver 130.

In addition, the transmission/reception switch 140 may transmit the reception signal received from the ultrasound probe 120 to the receiver 130 without attenuation in a receiving section in which the ultrasound probe 120 outputs the reception signal. As described above, since the receiver 130 may receive the reception signal without attenuation, the receiving performance of the ultrasound apparatus 100 is not degraded.

The transmission/reception switch 140 includes a switching module for blocking a transmission signal from being transmitted to the receiver 130 and allowing a reception signal to be transmitted to the receiver 130, and a resistor element for attenuating the transmission signal.

The transmission/reception switch 140 operates to disable the switching module in the transmitting section in which the transmitter 110 outputs the transmission signal such that the transmission signal is attenuated through the resistor element and is transmitted to the receiver 130, and enable the switching module in a receiving section in which the ultrasound probe 120 outputs the reception signal such that the reception signal is transmitted to the receiver 130 through the switching module without attenuation.

According to the operation of the transmission/reception switch 140 as described above, the receiver 130 may receive the attenuated transmission signal and the non-attenuated reception signal.

In addition, the receiver 130 may detect transmission waveform information on the basis of the attenuated transmission signal. The transmission waveform information is information about the transmission signal output from the transmitter 110, and may include at least one of the waveform of the transmission signal, the amplitude of the transmission signal, and information about a generation time of the transmission signal based on the synchronization signal, The controller 150 may control the operation of the internal components of the ultrasound apparatus 100. In detail, the controller 150 may control the transmitter 110 to output a transmission signal according to a transmission condition, and may control the ultrasound probe 120 to output a reception signal on the basis of the transmission signal.

In addition, the controller 150 may control the transmission/reception switch 140 to enable or disable the switching module between the transmitting section in which a transmission signal is output and the receiving section in which a reception signal is output, and may control the receiver 130 to receive a reception signal and am attenuated transmission signal.

The controller 150 may control the display 170 to display the ultrasound image acquired on the basis of the reception signal and the transmission waveform information acquired on the basis of the transmission signal to notify the user, and may receive a transmission condition from the user through the inputter 160 and store the received transmission condition.

The controller 150 may store a plurality of pieces of reference waveform information each corresponding to a plurality of transmission conditions, and compare detected transmission waveform information with reference waveform information having the same transmission condition as that of the detected transmission waveform information.

The controller 150 may continuously check whether the ultrasound apparatus 100 operates normally on the basis of a result of the comparison. When the detected transmission waveform information and the reference waveform information do not match each other, the controller 150 controls the display 170 to notify the user of the abnormality and stops operation of the ultrasound apparatus 100.

In addition, the controller 150 may correct the transmission signal corresponding to the detected transmission waveform information when the detected transmission waveform information and the reference waveform information do not match each other. In detail, the controller 150 may control the transmitter 110 to output a transmission signal having the same waveform as a reference waveform corresponding to a transmission condition of the transmission signal. The transmitter 110 may adjust a voltage gain or adjust an output delay time of a transmission signal on the basis of a control of the controller 150 to correct the transmission signal such that the transmission signal has the same waveform as that of the reference waveform corresponding to the transmission condition.

The controller 150 may compare the transmission waveform information corresponding to the corrected transmission signal with the reference waveform information. When the transmission waveform information corresponding to the corrected transmission signal and the reference waveform information do not match each other, the controller 150 controls the display 170 to notify the user of the abnormality, and stops operation of the ultrasound apparatus 100.

The inputter 160 may receive a command for starting diagnosis, selecting a diagnosis region, selecting a diagnosis type, and selecting a mode for an ultrasound image from the user. In detail, the inputter 160 may receive a transmission condition for a transmission signal output by the transmitter 110 from a user, and may transmit the transmission condition to the transmitter 110 through the controller 150.

The transmission condition may be varied according to the diagnostic region, the type of diagnosis, the mode for the ultrasound image, and the like, and in general, may include an amplitude magnitude of a transmission signal, a frequency of a transmission signal, and a generation time of a transmission signal based on a synchronization signal.

The display 170 may display the ultrasound image and the transmission waveform information according to the control signal of the controller 150. In addition, the display 170 may notify the user that the ultrasound apparatus 100 is abnormal based on the comparison result of the transmission waveform information and the reference waveform information. The display 170 may simultaneously display the ultrasound image and the transmission waveform information, and may display only the ultrasound image or the transmission waveform information according to the user's selection.

Referring to FIG. 2, the ultrasound apparatus 100 according to the embodiment includes the ultrasound probe 120 for transmitting an ultrasound signal to a target object, receiving an ultrasound echo signal reflected from the target object and converting the received ultrasound echo signal into an electrical signal, the main body 101, the inputter 160, and the display 170.

The ultrasound probe 120 may be connected to the main body 101 through the cable 180 to receive various signals required for controlling the ultrasound probe 120 or may transmit a reception signal corresponding to the ultrasound echo-signal received by the ultrasound probe 120 to the main body 101.

The reception signal may be one of an analog signal or a digital signal, which is converted into an electrical signal from an ultrasound echo signal by the ultrasound probe 120.

At least one female connector 195 may be provided at one side of the main body 101. The female connector 190 may be physically coupled to a male connector 190 provided at one end of the cable 180.

However, the embodiment of the ultrasound probe 120 is not limited thereto, and the ultrasound probe 120 may be connected to the body 101 in a wireless manner. In this case, the ultrasound probe 120 may be implemented as a wireless probe and transmit and receive signals through a network formed between the ultrasound probe 120 and the main body 101. In addition, a plurality of the ultrasound probes 120 may be connected to a single main body 101.

A plurality of casters 103 for moving the ultrasound apparatus 100 may be provided at the lower portion of the main body 101. The user may fix or move the ultrasound apparatus 100 using the plurality of casters 103. Such an ultrasound apparatus 100 is referred to as a cart-type ultrasound apparatus.

An operation panel 105 may be provided on the front surface of the main body 101. The operation panel 105 may include the inputter 160 for receiving a user's input, and a user may input a command for starting a diagnosis, selecting a diagnosis region, selecting a diagnosis type, and a mode for an ultrasound image through the inputter 160.

The display 170 may be provided on the upper portion of the main body 101. The display 170 may be implemented using at least one of display panels, such as a liquid crystal display (LCD) panel, a light emitting diode (LED) panel, and an organic light emitting diode (OLED).

In addition, the display 170 may include two or more displays, and the displays may simultaneously display different images. For example, one display may display a 2D ultrasound image and the other display may display a 3D ultrasound image. Alternatively, one display may display a B-mode image and the other display may display a contrast agent image. Alternatively, one display may display an ultrasound image, and the other display may display waveform information of a transmission signal.

The display 170 may display the ultrasound image based on the reception signal received from the ultrasound probe 120 and may display the waveform information of the transmission signal based on the transmission signal.

A user, including a medical practitioner, may perform diagnosis of a specific disease using the ultrasound image displayed on the display 170, and the site for which an ultrasound image is acquired may be varied according to the disease to be diagnosed.

In addition, the user, including a medical practitioner, may determine whether the ultrasound apparatus operates normally using the waveform information of the transmission signal displayed on the display 170, and may protect the patient from an abnormal operation of the ultrasound apparatus 100 and reduce the probability of misdiagnosis.

At least one probe holder for mounting the ultrasound probe 120 may be provided on the outer peripheral surface of the main body 101. Accordingly, when the ultrasound probe 120 is not used, the user may keep the ultrasound probe 120 on the probe holder.

The main body 101 may include the transmitter 110, the receiver 130, the transmission/reception switch 140, and the controller 150 built therein. The transmitter 110, the receiver 130, the transmission/reception switch 140, and the controller 150 may include at least one memory for storing a program for performing an operation of the ultrasound apparatus 100 and at least one processor for executing the stored program. The transmitter 110, the receiver 130, the transmission/reception switch 140, and the controller 150 may use separate memories and processors, or may share a memory and a processor.

Meanwhile, the external appearance of the ultrasound apparatus 100 according to the embodiment is not limited to the example shown in FIG. 2. When the ultrasound apparatus may be provided in a portable type, the main body 101 may have a form, such as a laptop computer, a personal digital assistant (PDA), a tablet PC, and the like, an ultrasound image may be generated by connecting the ultrasound probe 120 to the main body 101.

Figure 3:
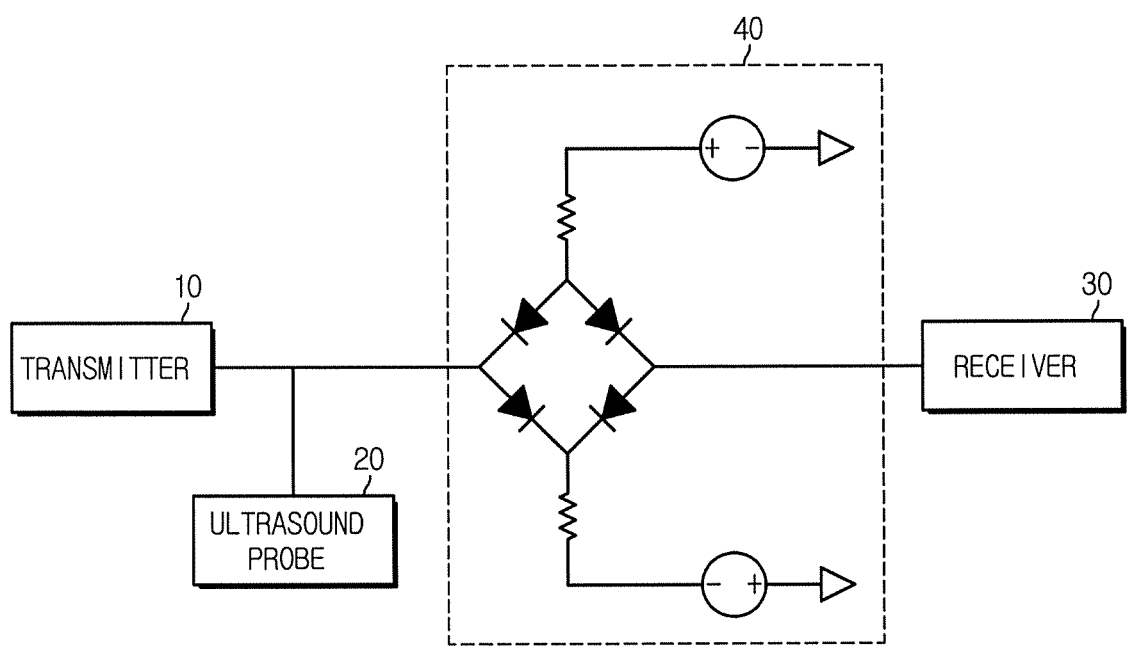
FIG. 3 is a circuit diagram illustrating a conventional ultrasound apparatus.
Figure 4:
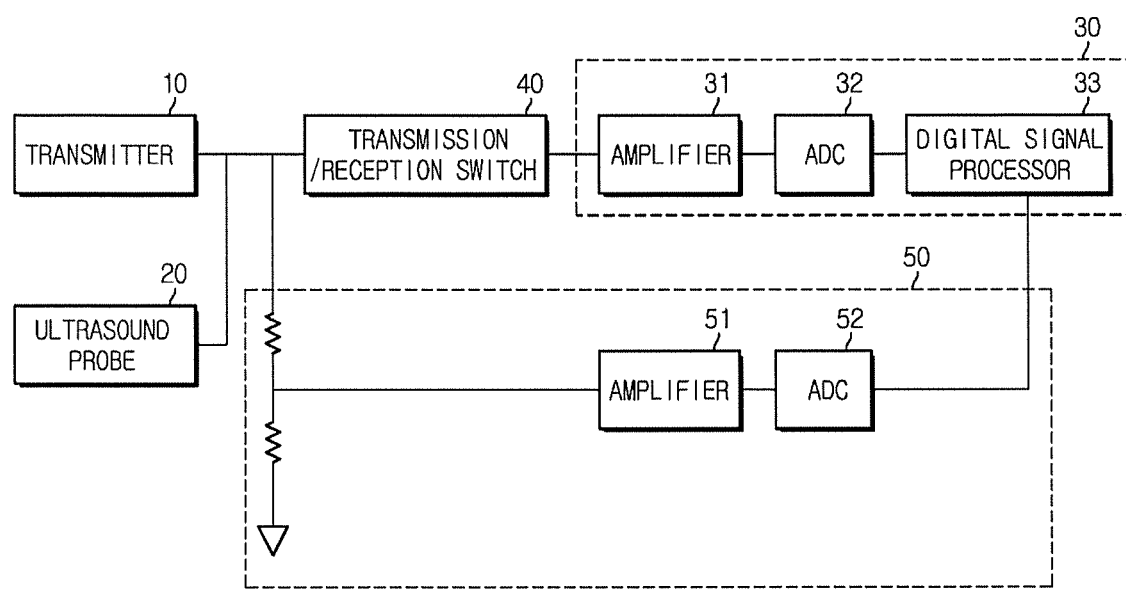
FIG. 4 is a block diagram illustrating a conventional ultrasound apparatus for acquiring a transmission waveform.

FIG. 3 is a circuit diagram illustrating a conventional ultrasound apparatus, and FIG. 4 is a block diagram illustrating a conventional ultrasound apparatus for acquiring a transmission waveform.

Referring to FIGS. 3 and 4, the conventional ultrasound apparatus includes a transmitter 10 for outputting a transmission signal to be converted into an ultrasound signal, an ultrasound probe 20 for transmitting the ultrasound signal to a target object and converting an ultrasound echo signal reflected from the target object into a reception signal and outputting the reception signal, an amplifier 31, an ADC 32, and a digital signal processor 33, and also includes a receiver 30 for receiving the reception signal and acquiring an ultrasound image, and a transmission/reception switch 40 for blocking the transmission signal and transmitting the reception signal.

The transmission/reception switch 40 of the conventional ultrasound apparatus blocks the transmission signal output from the transmitter 10 from being received by the receiver 30. In detail, the transmission/reception switch 40 connects the transmitter 10 to the ultrasound probe 20 in a transmitting section in which the transmitter 10 outputs the transmission signal, thereby transmitting the high-voltage transmission signal output from the transmitter 10 to the ultrasound probe 20 while completely isolating the receiver 30 from the high-voltage transmission signal.

In addition, the transmission/reception switch 40 connects the ultrasound probe 20 to the receiver 30 in a receiving section in which the ultrasound probe 20 outputs the receiving signal, thereby transmitting the reception signal provided from the ultrasound probe 20 to the receiver 30.

The transmission/reception switch 40 may include a diode bridge switchable between a first state and a second state. The transmission/reception switch 40 may operate to, in the first state, apply a reverse bias current to the diode bridge such that the transmission signal is blocked from being transmitted to the receiver 30, and in the second state, apply a forward bias current to the diode bridge such that the reception signal is transmitted to the receiver 30.

As such, the conventional ultrasound apparatus may block the transmission signal output from the transmitter 10 from being transmitted to the receiver 30. The transmission/reception switch 40 of the conventional ultrasound apparatus operates to block a high-voltage transmission signal output from the transmitter 10 from being transmitted to the receiver 30 to prevent the high-voltage transmission signal from breaking the receiver 30, which processes only a low-voltage signal, and to transmit only a low-voltage reception signal reflected from the human body to the receiver 30.

Accordingly, the conventional ultrasound apparatus is not able to check the waveform of the transmission signal in real time using the receiver 30, and thus require a separate reception circuit having the same number of attenuation circuits and ADCs as the number of transmission channels of the transmitter 10.

Referring to FIG. 4, in order to check the waveform of the transmission signal by the conventional ultrasound apparatus, there is a need to divide the voltage of the transmission signal at an output terminal of each transmission channel of the transmitter 10 using a resistor to reduce the voltage level, and then convert the transmission signal into a digital signal using an amplifier 51 and an ADC 52.

As such, in order to check the waveform of the transmission signal by the conventional ultrasound apparatus, the ultrasound apparatus needs to include not only the existing amplifier 31 and the existing ADC 32 on the receiver 30, but also the additional reception circuit 50 including the amplifier 51 and the ADC 52 for each transmission channel. With the amplifier 51 and the ADC 52 added for each transmission channel, the reception channel is doubled and thus the circuit size is increased.

Instead of having the additional amplifier 51 and the additional ADC 52 for each transmission channel, when a single amplifier and a single ADC connected to all the transmission channels may be provided, the transmission channels need to be enabled one by one when detecting the waveform of the transmission signal, which causes difficulty in detecting the waveform of the transmission signal in real time. Such a configuration may be used only to determine whether a pulser of each transmission channel operates normally for manufacturing or service purposes.

In addition, when a circuit for detecting a waveform of a transmission signal is not provided inside the ultrasound apparatus, the ultrasound apparatus needs to have a separate measuring device outside the ultrasound apparatus.

Figure 5:
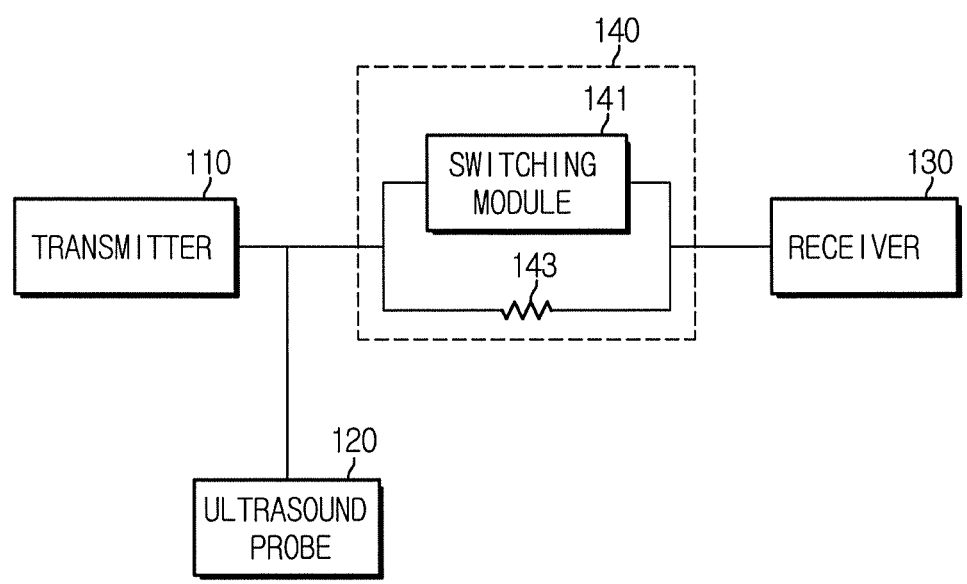
FIG. 5 is a block diagram illustrating an ultrasound apparatus according to an embodiment.
Figure 6:
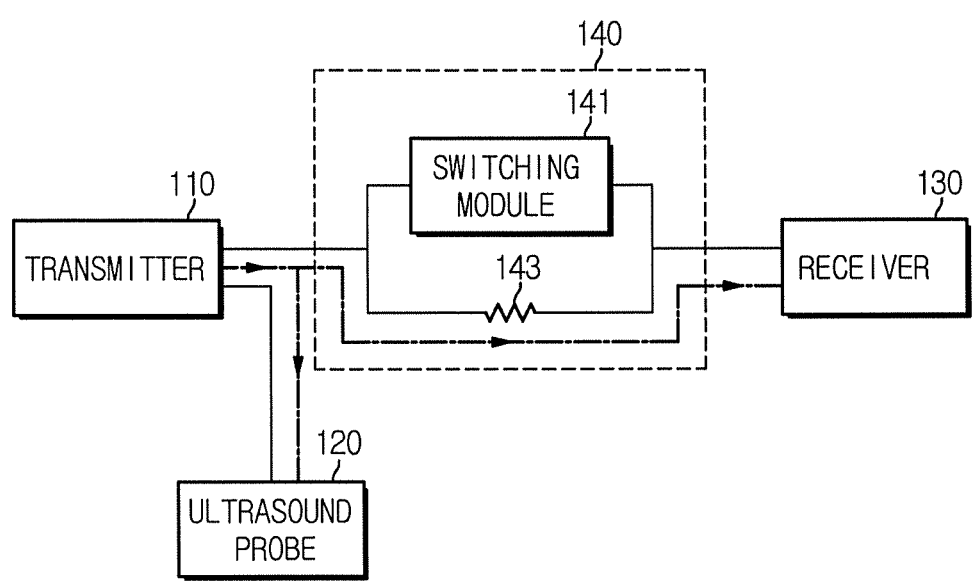
FIG. 6 is a view for describing a flow of a transmission signal in a transmitting section according to an embodiment.
Figure 7:
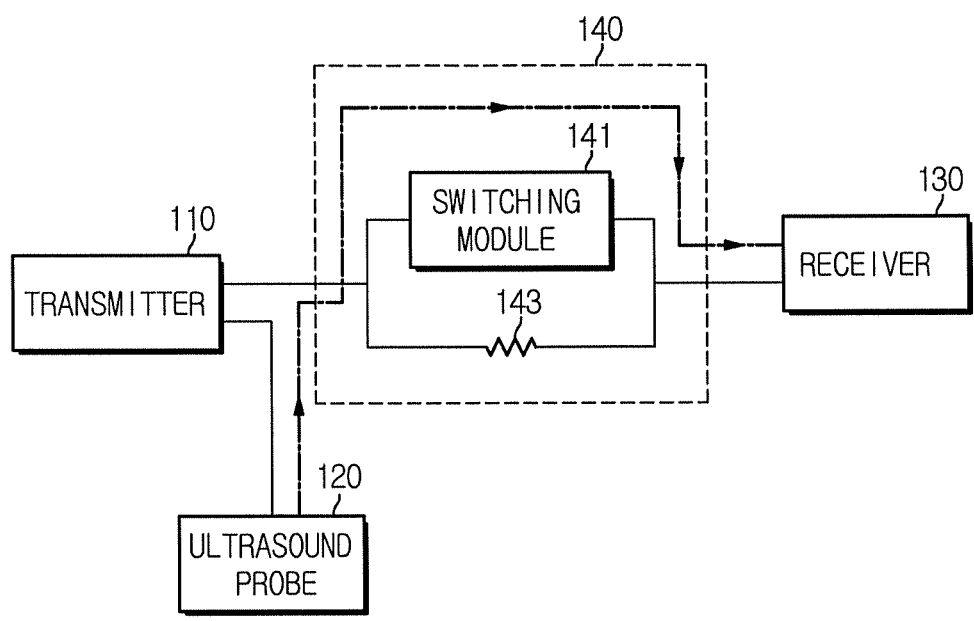
FIG. 7 is a diagram for describing a flow of a reception signal in a receiving section according to an embodiment.

FIG. 5 is a block diagram illustrating an ultrasound apparatus according to an embodiment, FIG. 6 is a view for describing a flow of a transmission signal in a transmitting section according to an embodiment, and FIG. 7 is a diagram for describing a flow of a reception signal in a receiving section according to an embodiment.

Referring to FIGS. 5, 6, and 7, the transmission/reception switch 140 may be connected to the transmitter 110, the ultrasound probe 120, and the receiver 130. In detail, one end of the transmission/reception switch 140 may be connected to the transmitter 110 and the ultrasound probe 120, and the other end of the transmission/reception switch 140 may be connected to the receiver 130.

The transmission/reception switch 140 may include a switching module 141 and a resistor element 143. The switching module 141 and the resistor element 143 may be arranged in parallel to each other and may be connected to the transmitter 110, the ultrasound probe 120, and the receiver 130.

The transmission/reception switch 140 may further include the resistor element 143 as compared to the transmission/reception switch 40 of the conventional ultrasound apparatus, and the switching module 141 of the transmission/reception switch 140 servers as the transmission/reception switch 40 of the conventional ultrasound apparatus.

In detail, the switching module 141 may serve to block the transmission signal output from the transmitter 110 while transmitting the reception signal output from the ultrasound probe 120 to the receiver 130. The resistor element 143 of the transmission/reception switch 140 is positioned between each terminal of the transmitter 110 and the receiver 130 to attenuate the voltage level of the transmission signal according to the input range of the receiver 130.

The transmission/reception switch 140 may operate to disable the switching module 141 in a transmitting section in which the transmitter 110 outputs a transmission signal, so that the transmission signal is attenuated through the resistor element 143 and the attenuated transmission signal is transmitted to the receiver 130, and enable the switching module 141 in a receiving section in which the ultrasound probe 120 outputs a reception signal so that the reception signal is transmitted to the receiver 130 through the switching module 141 without being attenuated.

Referring to FIG. 6, in the transmitting section in which the transmitter 110 transmits the transmission signal, the transmission signal is transmitted to the ultrasound probe 120 and is transmitted to the receiver 130 while being attenuated through the resistor element 143 of the transmission/reception switch 140.

In detail, in the transmitting section in which the transmitter 110 transmits the transmission signal, the transmission signal may be transmitted to the ultrasound probe 120. Since the resistor element 143 has a resistance value greater than an impedance of a transmission circuit including the ultrasound probe 120 and the cable 180, the transmission performance of the ultrasound apparatus 100 is not affected.

The transmission signal transmitted to the ultrasound probe 120 may be converted into an ultrasound signal by the transducer of the ultrasound probe 120. The converted ultrasound signal is transmitted from the ultrasound probe 120 to the target object and is reflected by the target object to form an ultrasound echo signal.

In the transmitting section in which the transmitter 110 transmits the transmission signal, the transmission signal may be transmitted to the receiver 130 through the resistor element 143. The transmission signal transmitted to the receiver 130 is a signal transmitted passing through the resistor 143, and is in a state attenuated according to the ratio of the input impedance of the receiver 130 and the resistor element 143. In detail, the voltage level of the transmission signal transmitted to the receiver 130 may be attenuated according to the ratio of the input impedance of the receiver 130 and the resistor element 143, as shown in Equation 1.

$$V_s' = V_s \times \frac{R_{in}}{R_s + R_{in}} \qquad \text{[Equation 1]}$$

In Equation 1, $V_s'$ denotes the voltage of the attenuated transmission signal, $V_s$ denotes the voltage of the transmission signal, $R_{in}$ denotes the input impedance of the receiver 130, and $R_s$ denotes the resistance value of the resistor element 143. The resistance value of the resistor element 143 may be set such that the voltage level of the transmission signal does not exceed the input range of the receiver 130.

The transmission signal output from the transmitter 110 may be transmitted to the transmission/reception switch 140. According to the embodiment, the transmission/reception switch 140 may disable the switching module 141 such that a transmission signal passes through to the resistor element 143 connected in parallel with the switching module 141. The state of the switching module 141 being disabled may represent an opened state in which the transmitter 110 is not connected to the receiver 130 through the switching module 141 such that both the transmission signal and the reception signal are blocked.

Accordingly, the transmission signal may be transmitted to the receiver 130 while being attenuated through the resistor element 143 only, without passing through the switching module 141. In addition, as the switching module 141 is disabled, the transmission signal that has not been attenuated may be completely blocked from being transmitted to the receiver 130.

The receiver 130 may receive the transmission signal attenuated through the resistor element 143 of the transmission/reception switch 140. The receiver 130 may process the attenuated transmission signal through the existing amplifier and the existing ADC without an additional amplifier and an additional ADC.

The attenuated transmission signal is amplified by the amplifier of the receiver 130, is converted into a digital signal by the ADC of the receiver 130, and is analyzed by the digital signal processor of the receiver 130. Accordingly, the receiver 130 may acquire transmission waveform information on the basis of the attenuated transmission signal. Such a configuration uses the existing reception signal path of the receiver 130 as it is, rather than requiring an additional reception channel.

Referring to FIG. 7, in a receiving section in which the ultrasound probe 120 outputs a reception signal, the reception signal may be transmitted to the receiver 130 through the switching module 141 of the transmission/reception switch 140.

In detail, in the receiving section in which the ultrasound probe 120 outputs the reception signal, the reception signal may be transmitted from the ultrasound probe 120 to the transmission/reception switch 140. The reception signal transmitted to the transmission/reception switch 140 may be transmitted to the receiver 130 through the switching module 141 of the transmission/reception switch 140, without being attenuated.

The transmission/reception switch 140 may operate to enable the switching module 141 such that the reception signal is transmitted to the receiver 130 through the switching module 141, without being attenuated. The state of the switching module 141 being enabled may represent a state of blocking the transmission signal and passing the reception signal.

Since the resistance value of the resistor element 143 is greater than the impedance when the switching module 141 is enabled, the reception performance of the ultrasound apparatus 100 is not affected. Accordingly, the reception signal may be transmitted to the receiver 130 through the switching module 141, without being attenuated through the resistor element 143.

The receiver 130 may receive the reception signal through the switching module 141 of the transmission/reception switch 140 without being attenuated. The receiver 130 may process the reception signal through an amplifier and an ADC. The reception signal is amplified by the amplifier of the receiver 130, is converted into a digital signal by the ADC of the receiver 130, and is analyzed by the digital signal processor of the receiver 130. Accordingly, the receiver 130 may acquire an ultrasound image through the reception signal.

Figure 8:
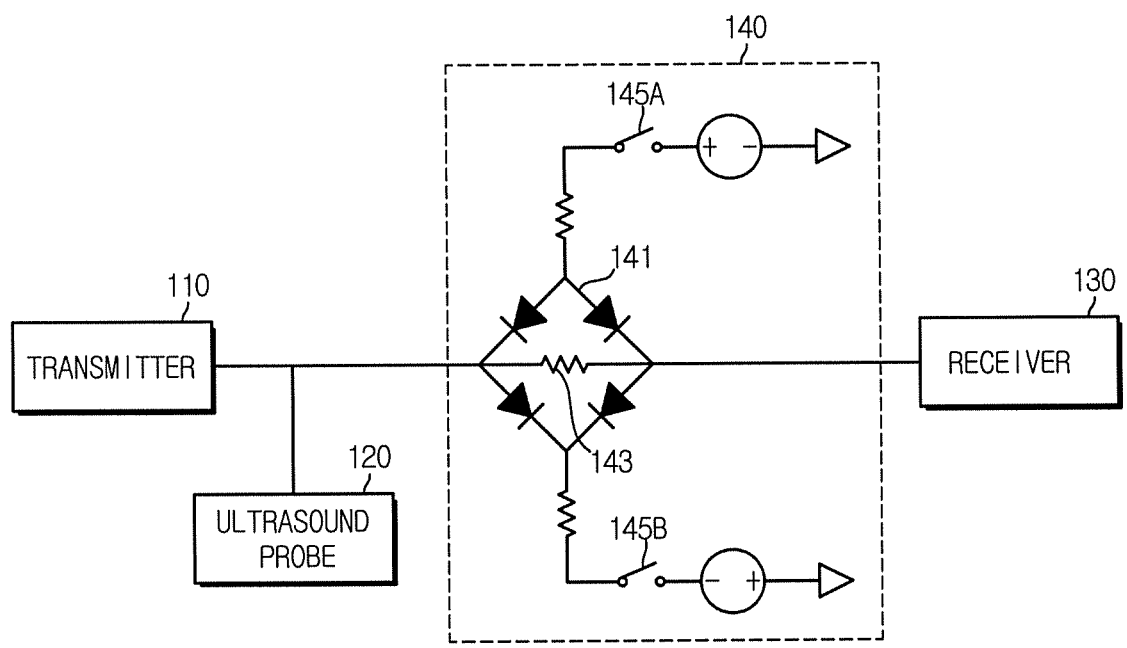
FIG. 8 is a circuit diagram of an ultrasound apparatus according to an embodiment.
Figure 9:
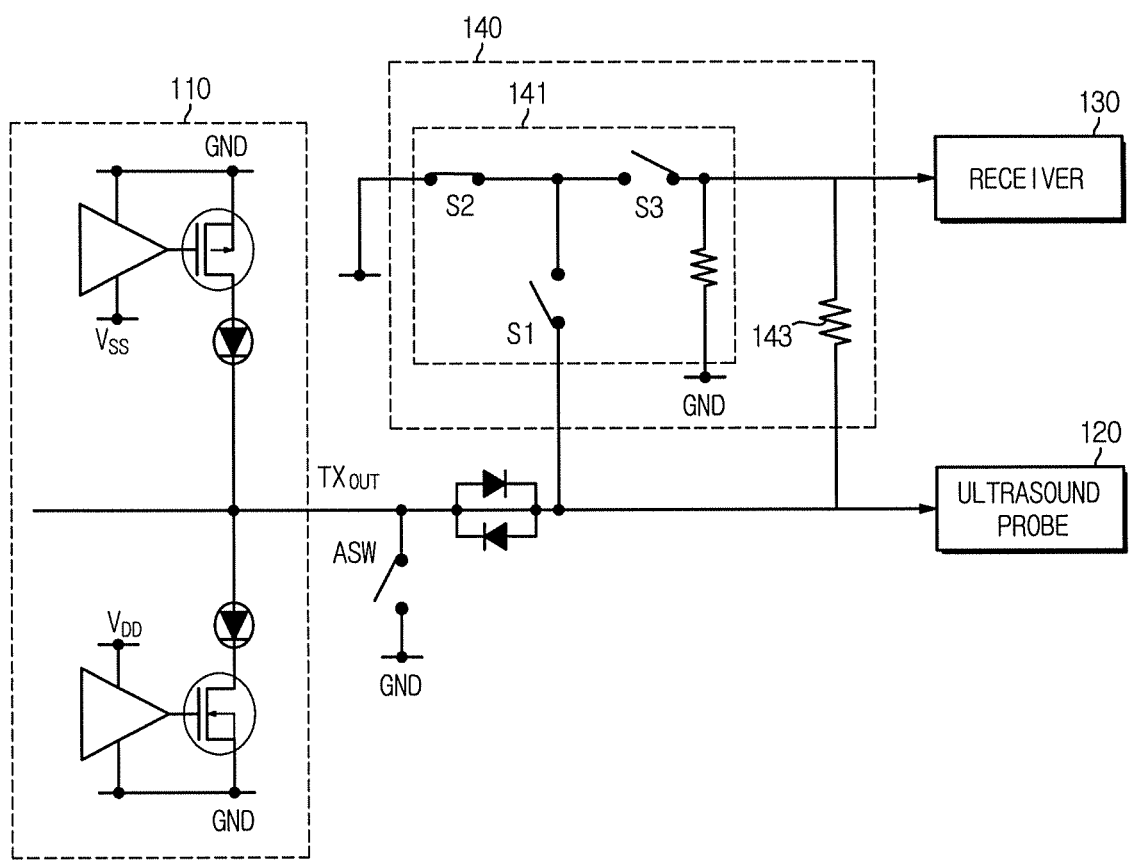
FIG. 9 is another circuit diagram of an ultrasound apparatus according to an embodiment.

FIG. 8 is a circuit diagram of an ultrasound apparatus according to an embodiment, and FIG. 9 is another circuit diagram of an ultrasound apparatus according to an embodiment.

Referring to FIG. 8, the ultrasound apparatus 100 includes a transmitter 110, an ultrasound probe 120, a receiver 130, and a transmission/reception switch 140. The transmission/reception switch 140 includes a switching module 141, a resistor element 143, a first switch 145A, and a second switch 145B.

The switching module 141 may include a diode bridge switchable between a first state and a second state. The switching module 141 is configured to, in the first state, apply a reverse bias current to the diode bridge to block the transmission signal from being transmitted to the receiver 130, and in the second state, apply a forward bias current to the diode bridge, to transmit the reception signal to the receiver 130.

To this end, the controller 150 may control a voltage source of the switching module 141 to apply a reverse bias current or a forward bias current to the diode bridge.

The resistor element 143 may be arranged in parallel with the switching module 141 and connected to the transmitter 110, the ultrasound probe 120, and the receiver 130. In detail, one end of the resistor element 143 is connected to the diode bridge, the transmitter 110, and the ultrasound probe 120, and the other end of the resistor element 143 is connected to the diode bridge and the receiver 130. The resistor element 143 may be positioned between the transmitter 110 and the receiver 130 to attenuate the voltage level of the transmission signal according to the input range of the receiver 130.

The transmission/reception switch 140 operates to disable the switching module 141 in a transmitting section in which the transmitter 110 outputs a transmission signal such that the transmission signal is attenuated through the resistor element 143 and is transmitted to the receiver 130, and enable the switching module 141 in a receiving section in which the ultrasound probe 120 outputs a reception signal such that the reception signal is transmitted to the receiver 130 through the switching module 141 without being attenuated.

The first switch 145A and the second switch 145B of the transmission/reception switch 140 may operate to switching between disabling and enabling the switching module 141.

In detail, the first switch 145A and the second switch 145B are opened in the transmitting section in which the transmitter 110 outputs the transmission signal, disabling the switching module 141. Accordingly, the transmission signal and the reception signal may not be transmitted to the receiver 130 through the switching module 141.

In addition, the first switch 145A and the second switch 145B may be short-circuited in the receiving section in which the ultrasound probe 120 outputs the reception signal, enabling the switching module 141. Accordingly, the transmission signal is blocked from being transmitted to the receiver 130, and the reception signal is transmitted to the receiver 130.

Referring to FIG. 9, the ultrasound apparatus 100 includes a transmitter 110, an ultrasound probe 120, a receiver 130, and a transmission/reception switch 140. The transmission/reception switch 140 includes a switching module 141 and a resistor element 143.

The switching module 141 may include switches S1, S2, and S3 that are switchable between a first state and a second state. The switching module 141 may control each of the switches S1, S2, and S3 to operate in one of an opened state and a short-circuited state. In addition, the switches S1, S2, and S3 of the switching module 141 may be controlled by the controller 150.

The switching module 141 may operate to, in the first state, adjust at least one of the switches S1 and S3 to be opened such that the transmitter 110 is not connected to the receiver 130 through the switching module 141, to thereby block the transmission signal from being transmitted to the receiver 130, and in the second state, adjust the switch S1 and the switch S3 to be short-circuited and adjust the switch S1 to be opened such that the transmitter 110 is connected to the receiver 130 through the switching module 141, to thereby transmit the reception signal to the receiver 130.

Although the switching module 141 shown in FIG. 9 is illustrated as having three switches S1, S2, and S3, the disclosed embodiments are described for illustrative purposes and not for limiting purposes.

The transmission/reception switch 140 operates to disable the switching module 141 in a transmitting section in which the transmitter 110 outputs a transmission signal such that the transmission signal is attenuated through the resistor element 143 and is transmitted to the receiver 130, and enable the switching module 141 in a receiving section in which the ultrasound probe 120 outputs a reception signal such that the reception signal is transmitted to the receiver 130 through the switching module 141 without being attenuated.

In the disabled state of the switching module 141, at least one switch is adjusted such that the transmitter 110 is not connected to the receiver 130 through the switching module 141, and in the enabled state, at least one switch is adjusted such that the transmission signal is prevented from being transmitted to the receiver 130 and the reception signal is transmitted to the receiver 130.

Figure 10:
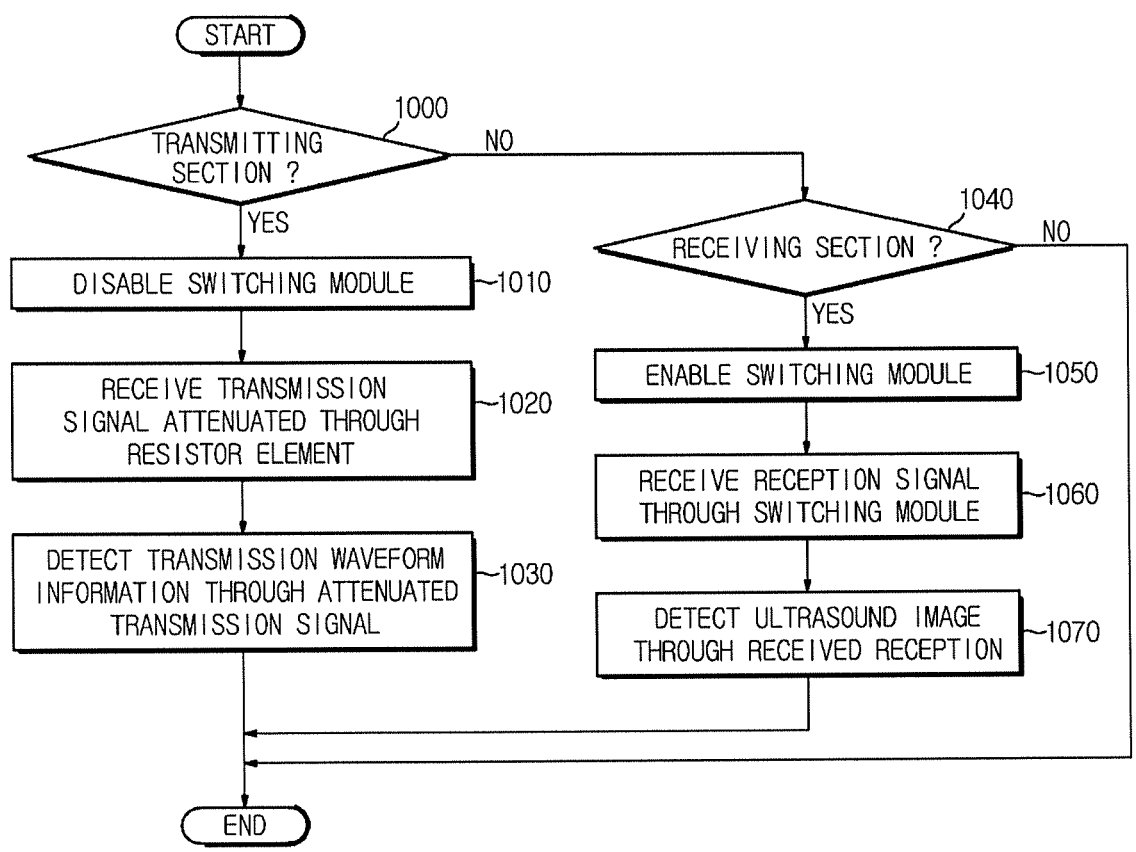
FIG. 10 is a flowchart showing a method of controlling an ultrasound apparatus according to an embodiment.
Figure 11:
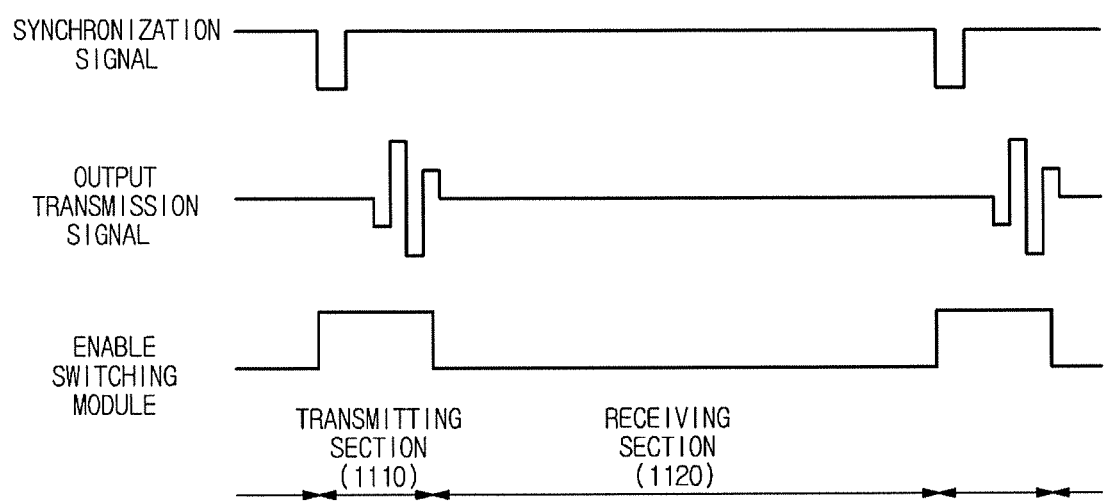
FIG. 11 is a view for describing a transmitting section and a receiving section according to an embodiment.
Figure 12A:
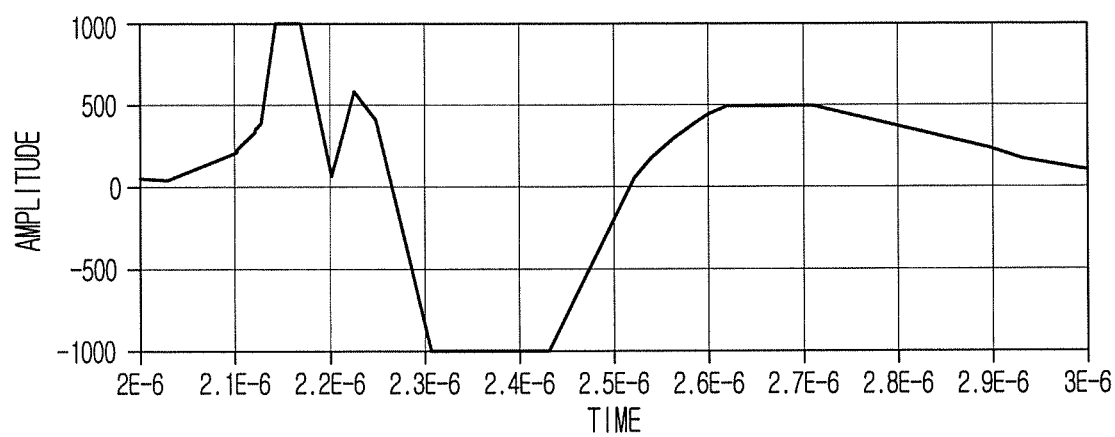
FIG. 12a and FIG. 12b are graphs showing a transmission waveform according to an embodiment.
Figure 12B:
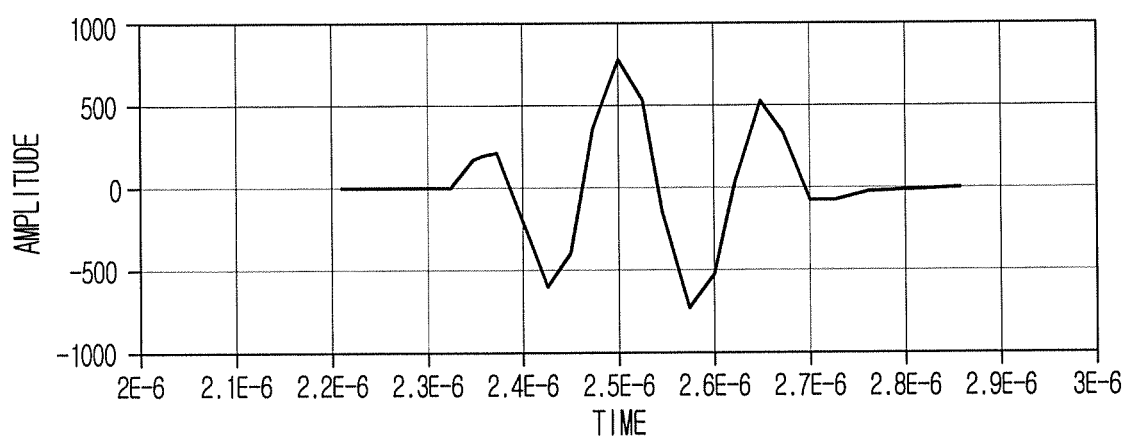

FIG. 10 is a flowchart showing a method of controlling an ultrasound apparatus according to an embodiment, FIG. 11 is a view for describing a transmitting section and a receiving section according to an embodiment, and FIG. 12a and FIG. 12b are graphs showing a transmission waveform according to an embodiment.

Referring to FIG. 10, the ultrasound apparatus 100 according to an embodiment may check whether the current section is a transmitting section (1000). In the transmitting section, the transmitter 110 of the ultrasound apparatus 100 may output a transmission signal. In addition, according to an embodiment, the transmitting section may include a section in which a synchronization signal serving as a reference for outputting a transmission signal is output.

When the current section is the transmitting section in which the transmitter 110 outputs the transmission signal (YES in 1000), the ultrasound apparatus 100 may disable the switching module 141 of the transmission/reception switch 140 (1010).

In detail, when it is confirmed that the ultrasound apparatus 100 is in the transmitting section, the controller 150 of the ultrasound apparatus 100 may control the switching module 141 to be disabled. The state of the switching module 141 being disabled may represent a state in which the transmitter 110 is not connected to the receiver 130 through the switching module 141.

Referring to FIG. 11, the transmitter 110 may output a transmission signal at a time delay that is set on the basis of a synchronization signal having a pulse repetition frequency (PRF). In the case of a transmitting section 1110 including a section in which a synchronization signal is output and a section in which a transmission signal is output, the switching module 141 of the transmission/reception switch 140 may be disabled.

When the switching module 141 is disabled, the ultrasound apparatus 100 may receive the transmission signal attenuated through the resistor element 143 (1020). In detail, the transmission signal output from the transmitter 110 may be received by the receiver 130 while being attenuated through the resistor element 143 of the transmission/reception switch 140. The voltage level of the attenuated transmission signal may be a voltage level attenuated not to exceed the input range of the receiver 130.

The ultrasound apparatus 100 may detect the transmission waveform information through the attenuated transmission signal (1030). In detail, the receiver 130 of the ultrasound apparatus 100 may receive the attenuated transmission signal and analyze the attenuated transmission signal to detect the transmission waveform information. The receiver 130 amplifies the attenuated transmission signal by an amplifier, converts the attenuated transmission signal into a digital signal by the ADC, and analyzes the digital signal by the digital signal processor.

The transmission waveform information may include at least one of the waveform of the transmission signal, the amplitude of the transmission signal, the frequency of the transmission signal, and information about the generation time of the transmission signal based on the synchronization signal. The controller 150 of the ultrasound apparatus 100 may control the display 170 to display the detected transmission waveform information.

Referring to FIG. 12a and FIG. 12b, the display 170 may display the detected transmission waveform information according to the embodiment. FIG. 12a shows a waveform of a transmission signal obtained by using the conventional transmission/reception switch 40. The conventional transmission/reception switch 40 is intended to block the transmission signal, and thus has a difficulty in receiving the transmission signal without distortion. Since the waveform of the transmission signal obtained by using the conventional transmission/reception switch 40 is distorted by the blocking operation of the transmission/reception switch 40, the waveform of the transmission signal, the amplitude of the transmission signal, information about the generation time of the transmission signal based on the synchronization signal may not be identified.

FIG. 12b shows a waveform of a transmission signal obtained using the transmission/reception switch 140 according to the embodiment. The receiver 130 receives the transmission signal attenuated through the resistor element 143 of the transmission/reception switch 140, and thus is able to detect the waveform of the transmission signal, the amplitude and frequency of which are not impaired.

In detail, the user may identify the amplitude of the transmission signal including the peak value of the voltage through the waveform of the transmission signal obtained using the transmission/reception switch 140 according to the embodiment, and identify information about the generation time of the transmission signal based on the synchronization signal.

In addition, the user may identify the frequency of the transmission signal through the waveform variation over time. The user may check whether the voltage of the transmission signal is within an intended range through the waveform and the amplitude of the transmission signal.

In addition, since the user may obtain not only the waveform of the transmission signal but also the information about the generation time of the transmission signal based on the transmission synchronization signal, the transmission focusing state is also identified.

As such, the ultrasound apparatus 100 may measure the amplitude and transmission timing of the transmission signal for each transmission channel by analyzing the transmission signal in real time. Accordingly, the user of the ultrasound apparatus 100 is protected from the heat generated from the surface of the ultrasound probe 120 due to the abnormal output of the transmission signal and the transient energy of the ultrasound signal irradiated to the human body.

In addition, the degradation of the performance of the ultrasound apparatus 100 caused when the transmission signal is transmitted in an unintended manner is prevented, thereby preventing diagnosis errors and the like.

Referring again to FIG. 10, when the current section is not a transmitting section in which the transmitter 110 outputs a transmission signal (NO in 1000), the ultrasound apparatus 100 may check whether the current section is a receiving section (1040). In the receiving section, the ultrasound probe 120 may output a reception signal based on an ultrasound echo signal reflected from the target object.

When the current section is a receiving section in which the ultrasound probe 120 outputs a reception signal (YES in 1040). the ultrasound apparatus 100 may enable the switching module 141 of the transmission/reception switch 140 (1050)

In detail, when it is confirmed that the ultrasound apparatus 100 is in the receiving section, the controller 150 of the ultrasound apparatus 100 may control the switching module 141 to be enabled. The state of the switching module 141 being enabled may represent a state in which the transmitter 110 is connected to the receiver 130 through the switching module 141. In detail, the switching module 141, when enabled, operates to block the transmission signal from being transmitted to the receiver 130 and allow the reception signal to be transmitted to the receiver 130.

Referring to FIG. 11, the switching module 141 may be enabled in a receiving section 1120 in which the ultrasound probe 120 outputs a reception signal. In detail, in the case of the receiving section 1120 rather than the transmitting section 1110, the switching module 141 of the transmission/reception switch 140 may be enabled.

When the switching module 141 is enabled, the ultrasound apparatus 100 may receive the reception signal through the switching module 141 (1060). In detail, the reception signal output from the ultrasound probe 120 may be received by the receiver 130 through the switching module 141 of the transmission/reception switch 140 without being attenuated.

The ultrasound apparatus 100 may detect an ultrasound image through the received reception signal (1070). In detail, the receiver 130 of the ultrasound apparatus 100 may receive the attenuated transmission signal and analyze the attenuated transmission signal to detect the transmission waveform information.

The receiver 130 amplifies the reception signal by the amplifier, converts the amplified signal into a digital signal by the ADC, and analyzes the digital signal by a digital signal processor. Accordingly, the receiver 130 may detect the ultrasound image based on the reception signal. The controller 150 of the ultrasound apparatus 100 may control the display 170 to display the detected ultrasound image.

Since the ultrasound apparatus 100 disables the switching module 141 in the transmitting section and enables the switching module 141 in the receiving section, the ultrasound apparatus 100 may perform the transmission error detection in the operation of the ultrasound apparatus 100 in real time.

Figure 13:
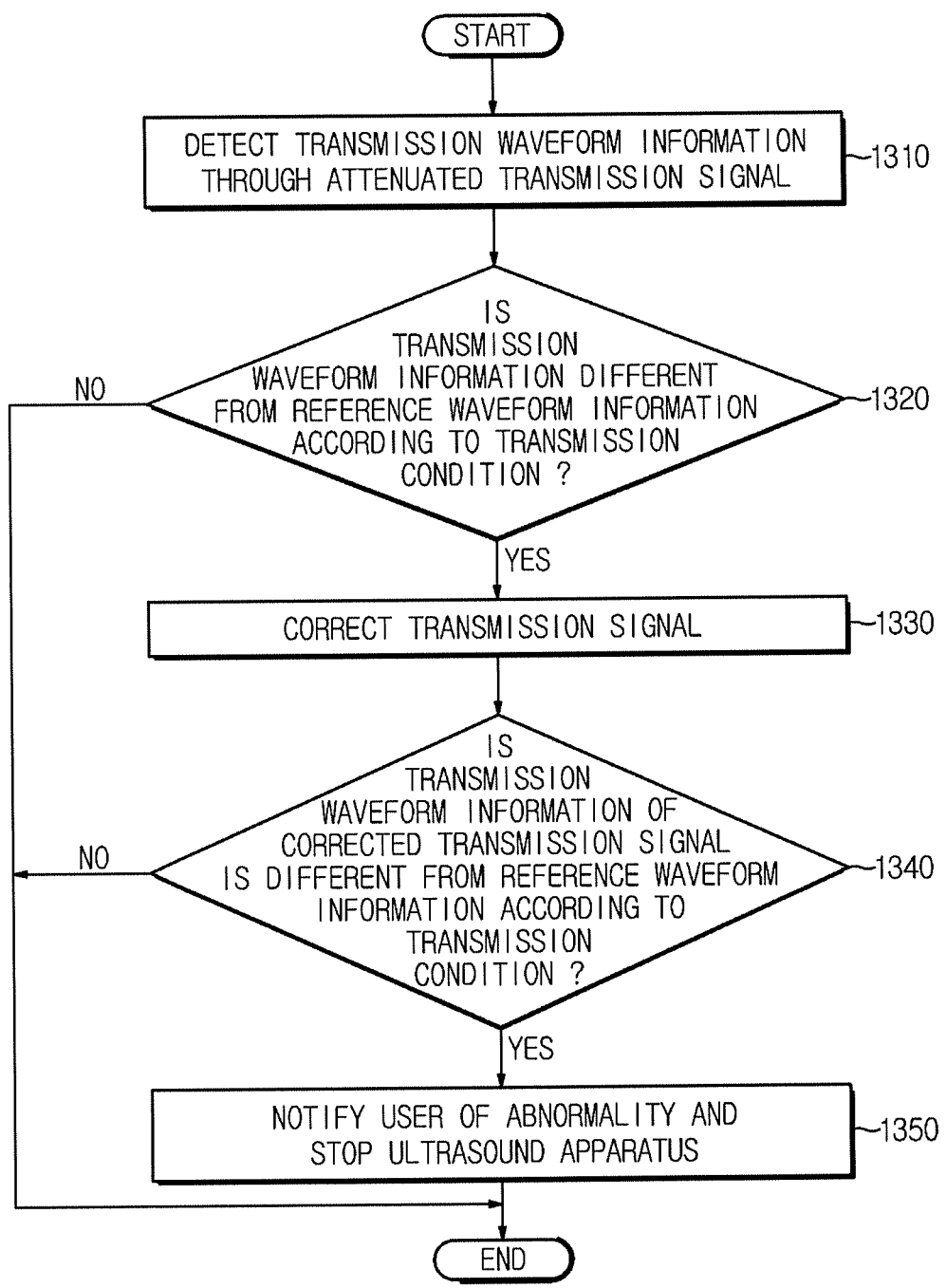
FIG. 13 is a flowchart showing a method of controlling an ultrasound apparatus according to an embodiment.

FIG. 13 is a flowchart showing a method of controlling an ultrasound apparatus according to an embodiment.

Referring to FIG. 13, the ultrasound apparatus 100 may detect transmission waveform information through an attenuated transmission signal (1310). In detail, the receiver 130 of the ultrasound apparatus 100 may receive a transmission signal that is output from the transmitter 110 and is attenuated through the resistor element 143 of the transmission/reception switch 140.

The receiver 130 amplifies the attenuated transmission signal by the amplifier, converts the amplified transmission signal into a digital signal by the ADC, and analyzes the digital signal by the digital signal processor, to thereby detect transmission waveform information.

The ultrasound apparatus 100 may check whether the transmission waveform information is different from reference waveform information according to a transmission condition (1320). In detail, the controller 150 of the ultrasound apparatus 100 may receive transmission waveform information obtained from the receiver 130, and determine whether the transmission waveform information is different from reference waveform information according to a transmission condition. The controller 150 may compare the waveform of the transmission signal, the amplitude of the transmission signal, and the information about the generation time of the transmission signal based on the synchronization time with the reference waveform information.

Accordingly, the controller 150 of the ultrasound apparatus 100 may continuously check whether the ultrasound apparatus 100 operates normally or not on the basis of a result of the comparison. Whether the ultrasound apparatus 100 operates normally or not is checked whenever the transmission condition is changed, so that the stability may be ensured.

To this end, the controller 150 may store a plurality of pieces of reference waveform information each corresponding to a plurality of transmission conditions. The reference waveform information represents information about a transmission waveform intended by the user in a corresponding transmission condition.

The transmission condition may be input through the inputter 160 as a condition for a transmission signal intended by the user. The transmission condition may be varied according to the diagnosis region, the type of diagnosis, the mode for the ultrasound image, and the like. In general, the transmission condition may include an amplitude magnitude of a transmission signal, a frequency of a transmission, a generation time of a transmission signal based on a synchronization signal, and the like.

The ultrasound apparatus 100 may be configured to, when the transmission waveform information is different from the reference waveform information (YES in 1320), correct a transmission signal corresponding to the detected transmission waveform information (1330). In detail, when detected transmission waveform information is different from reference waveform information according to a transmission condition, the controller 150 of the ultrasound apparatus 100 may control the transmitter 110 to output a transmission signal having the same waveform information as the reference waveform information corresponding to the transmission condition.

The transmitter 110 may correct the transmission signal by adjusting the voltage gain or the output delay time of the transmission signal on the basis of the control of the controller 150 such that the transmission signal has the same waveform information as the reference waveform information corresponding to the transmission condition. Accordingly, a plurality of transmission channels of the ultrasound apparatus 100 may output transmission signals having uniform magnitudes of waveforms between the channels.

According to another embodiment, the controller 150 of the ultrasound apparatus 100 may control the display 170 to notify the user of the abnormality when the transmission waveform information is different from the reference waveform information (YES in 1320), and stop operation of the ultrasound apparatus 100.

The ultrasound apparatus 100 may check whether the corrected transmission waveform information is different from the reference waveform information according to the transmission condition (1340). In detail, the controller 150 of the ultrasound apparatus 100 may receive the corrected transmission waveform information from the receiver 130 and determine whether the corrected transmission waveform information is different from the reference waveform information according to the transmission condition. Accordingly, the ultrasound apparatus 100 may check whether the transmission signal output from the transmitter 110 is output according to the intended transmission condition.

When the corrected transmission waveform information is different from the reference waveform information according to the transmission condition (YES in 1340), the ultrasound apparatus 100 may control the display 170 to notify the user of the abnormality and stop operation of the ultrasound apparatus 100 (1350).

In detail, the controller 150 of the ultrasound apparatus 100 confirms that the ultrasound apparatus 100 operates abnormally when the waveform of the corrected transmission signal output from the transmitter 110 is different from the reference waveform according to the transmission condition, notifies the user of the abnormality of the ultrasound apparatus 100 through the display 170, and stops operation of the ultrasound apparatus 100.

According to another embodiment, when the corrected transmission waveform information is different from the reference waveform information according to the transmission condition, the ultrasound apparatus 100 may correct the transmission signal corresponding to the corrected transmission waveform information once again. Although FIG. 13 illustrates an example in which the process of correcting the transmission signal is performed once, the disclosed embodiment is merely an example, and the process of correcting the transmission signal may be performed one or more times according to the setting of the user.

As is apparent from the above, the ultrasound apparatus and control method thereof according to an aspect of the present disclosure can detect a waveform of a transmission waveform in real time using a reception channel for receiving a reception signal output from a ultrasound probe without an additional reception channel.

Although exemplary embodiments of the present disclosure have been described for illustrative purposes, those skilled in the art will appreciate that various modifications, additions and substitutions are possible, without departing from the scope and spirit of the disclosure. Therefore, exemplary embodiments of the present disclosure have not been described for limiting purposes.

What is claimed is:

1. An ultrasound apparatus comprising:
    a transmitter configured to generate and output a transmission signal;
    an ultrasound probe configured to convert the transmission signal output from the transmitter into an ultrasound signal and transmit the ultrasound signal to a target object, and receive an echo signal reflected from the target object and output a reception signal on the basis of the echo-signal;
    a transmission/reception switch configured to attenuate the transmission signal output from the transmitter and output the attenuated transmission signal, and output the reception signal output from the ultrasound probe; and
    a receiver configured to receive the attenuated transmission signal output and the output reception signal, and detect transmission waveform information on the basis of the attenuated transmission signal.

2. The ultrasound apparatus of claim 1, wherein the transmission/reception switch includes a switching module configured to block the transmission signal from being transmitted to the receiver and allow the reception signal to be transmitted to the receiver; and
    a resistor element configured to attenuate the transmission signal.

3. The ultrasound apparatus of claim 2, wherein the switching module includes a diode bridge switchable between a first state and a second state.

4. The ultrasound apparatus of claim 3, wherein the switching module blocks the transmission signal from being transmitted to the receiver by applying a reverse bias current to the diode bridge in the first state, and allows the reception signal to be transmitted to the receiver by applying a forward bias current to the diode bridge in the second state.

5. The ultrasound apparatus of claim 2, wherein the switching module includes at least one switch that is switchable between a first state and a second state.

6. The ultrasound apparatus of claim 5, wherein the switching module controls the at least one switch to operate in one of a short-circuit state and an open-circuit state, to block the transmission signal from being transmitted to the receiver in the first state and allow the transmission signal to be transmitted to the receiver in the second state.

7. The ultrasound apparatus of claim 2, wherein the transmission/reception switch is configured to:
disable the switching module in a first section such that the transmission signal is attenuated through the resistor element and is transmitted to the receiver; and
enable the switching module in a second section such that the reception signal is transmitted to the receiver through the switching module,
wherein the first section is a section in which the transmitter outputs the transmission signal, and the second section is a section in which the ultrasound probe outputs the reception signal.

8. The ultrasound apparatus of claim 2, wherein the attenuated transmission signal has a voltage that is defined as Equation 1, in which the voltage of the attenuated transmission signal falls within an input range of the receiver:

$$V'_s = V_s \times \frac{R_{in}}{R_s + R_{in}},$$ [Equation 1]

in Equation 1, $V'_s$ denotes a voltage of the attenuated transmission signal, $V_s$ denotes a voltage of the transmission signal, $R_{in}$ denotes an input impedance of the receiver, and $R_s$ denotes a resistance value of the resistor element.

9. The ultrasound apparatus of claim 1, wherein the transmission waveform information includes at least one of a waveform of the transmission signal, an amplitude of the transmission signal, and information about a generation time of the transmission signal based on a synchronization signal.

10. An ultrasound apparatus comprising:
a transmitter configured to generate and output a transmission signal;
an ultrasound probe configured to convert a transmission signal output from the transmitter into an ultrasound signal and transmit the ultrasound signal to a target object, and receive an echo signal reflected from the target object and output a reception signal on the basis of the echo-signal;
a transmission/reception switch configured to attenuate the transmission signal output from the transmitter and output the attenuated transmission signal, and output the reception signal output from the ultrasound probe; and
a receiver configured to receive the attenuated transmission signal output and the output reception signal, and detect transmission waveform information on the basis of the attenuated transmission signal;
a display; and
a controller configured to store reference waveform information according to a transmission condition, and compare the detected transmission waveform information with the reference waveform information.

11. The ultrasound apparatus of claim 10, wherein the controller, when the detected transmission waveform information is different from the reference waveform information, controls the display to notify a user of an abnormality, or stops operating the ultrasound apparatus.

12. The ultrasound apparatus of claim 10, wherein the controller, when the detected transmission waveform information is different from the reference waveform information, corrects the transmission signal corresponding to the detected transmission waveform information.

13. The ultrasound apparatus of claim 12, wherein the controller compares transmission waveform information corresponding to the corrected transmission signal with the reference waveform information.

14. The ultrasound apparatus of claim 13, wherein the controller, when the transmission waveform information is different from the reference waveform information, controls the display to notify a user of an abnormality, or stops operating the ultrasound apparatus.

15. The ultrasound apparatus of claim 10, wherein the controller controls the display to display the detected transmission waveform information.

16. The ultrasound apparatus of claim 1, wherein one end of the transmission/reception switch is connected to the transmitter and the ultrasound probe, and an opposite end of the transmission/reception switch is connected to the receiver.

17. A method of controlling an ultrasound apparatus including a ultrasound probe and a transmission/reception switch, the method comprising:
receiving a transmission signal output from a transmitter and a reception signal output from the ultrasound probe by controlling the transmission/reception switch;
outputting the transmission signal attenuated by a resistor element by controlling the transmission/reception switch;
outputting the reception signal through a switching module by controlling the transmission/reception switch;
receiving the attenuated transmission signal output and the output reception signal by controlling a receiver; and
detecting transmission wave information on the basis of the attenuated transmission signal by controlling the receiver.

18. The method of claim 17, further comprising:
disabling the switching module in a first section such that the transmission signal is attenuated through the resistor element and is transmitted to the receiver; and
enabling the switching module in a second section such that the reception signal is transmitted to the receiver through the switching module,
wherein the first section is a section in which the transmitter outputs the transmission signal, and the second section is a section in which the ultrasound probe outputs the reception signal,
wherein the second section is different from the first section.

19. The method of claim 17, further comprising:
storing reference waveform information according to a transmission condition; and
comparing the detected transmission waveform information with the reference waveform information.

20. The method of claim 19, further comprising: when the detected transmission waveform information is different from the reference waveform information, controlling a display to notify a user of an abnormality or stopping operating the ultrasound apparatus.

\* \* \* \* \*